United States Patent
Otani et al.

(10) Patent No.: US 7,526,942 B2
(45) Date of Patent: May 5, 2009

(54) CONTACT COMBUSTION GAS SENSOR

(75) Inventors: Seiichi Otani, Tokyo (JP); Mamoru Furusato, Tokyo (JP); Yoshikazu Shibasaki, Tokyo (JP); Shoei Yasuda, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 292 days.

(21) Appl. No.: 10/560,359

(22) PCT Filed: Jun. 4, 2004

(86) PCT No.: PCT/JP2004/007827

§ 371 (c)(1), (2), (4) Date: Dec. 12, 2005

(87) PCT Pub. No.: WO2004/111628

PCT Pub. Date: Dec. 23, 2004

(65) Prior Publication Data

US 2006/0133962 A1    Jun. 22, 2006

(30) Foreign Application Priority Data

Jun. 12, 2003 (JP) ............................ 2003-168042
Jun. 13, 2003 (JP) ............................ 2003-168614

(51) Int. Cl.
*G01N 33/00* (2006.01)
(52) U.S. Cl. .................. 73/25.03; 73/25.05; 422/95; 422/97
(58) Field of Classification Search ........... 73/25.05, 73/25.03, 25.01; 422/95, 97
See application file for complete search history.

(56) References Cited

U.S. PATENT DOCUMENTS

| | | | | |
|---|---|---|---|---|
| 3,564,474 A * | 2/1971 | Firth | ............ | 338/25 |
| 3,644,795 A * | 2/1972 | Taguchi | ............ | 361/526 |
| 4,259,292 A * | 3/1981 | Ichinose et al. | ............ | 422/98 |
| 4,303,612 A * | 12/1981 | Sonley | ............ | 422/94 |
| 4,327,054 A * | 4/1982 | Yasuda et al. | ............ | 422/95 |
| 4,337,028 A * | 6/1982 | Angwin et al. | ............ | 431/7 |
| 4,447,397 A * | 5/1984 | Anouchi et al. | ............ | 422/94 |
| 4,464,339 A * | 8/1984 | Wilkinson-Tough | ............ | 422/94 |
| 4,469,626 A * | 9/1984 | Tuohig et al. | ............ | 252/514 |
| 4,723,439 A * | 2/1988 | Asakura et al. | ............ | 73/29.05 |
| 5,629,474 A * | 5/1997 | Williams | ............ | 73/23.2 |
| 5,756,207 A * | 5/1998 | Clough et al. | ............ | 428/375 |
| 5,964,089 A * | 10/1999 | Murphy et al. | ............ | 60/286 |
| 5,969,232 A * | 10/1999 | Schonauer et al. | ............ | 73/31.05 |
| 6,019,946 A * | 2/2000 | Castillo et al. | ............ | 422/94 |
| 6,143,928 A * | 11/2000 | Karim et al. | ............ | 562/534 |
| 6,156,928 A * | 12/2000 | Karim et al. | ............ | 562/548 |
| 6,261,990 B1* | 7/2001 | Terada et al. | ............ | 502/325 |
| 6,461,751 B1* | 10/2002 | Boehm et al. | ............ | 429/13 |

OTHER PUBLICATIONS

Moseley, P.T. and Tofield, B. C., Solid State Gas Sensors, 1987, p. 20.*
Derwent abstract for JP 03172749 A, 1991.*

* cited by examiner

*Primary Examiner*—Daniel S Larkin
(74) *Attorney, Agent, or Firm*—Connolly Bove Lodge & Hutz LLP (57) ABSTRACT

A contact combustion-type gas sensor that can maintain its initial sensitivity over a long period of time in the presence of silicon vapor, wherein an induction portion 5 of a gas detecting element 1 contains not less than 30 percent by weight of an oxidation catalyst, and is aged in advance in an environment that contains silicon vapor serving as a poisoning substance.

10 Claims, 7 Drawing Sheets

Surface side

Interior side (B)

Surface side

Interior side

⊘ : Oxidation catalyst particles covered by silicon compounds

CONTACT COMBUSTION GAS SENSOR

This application is the U.S. National Stage under 35 U.S.C. 371 of PCT/JP2004/007827 which in turn claims priority from Japanese application 2003-168042 filed Jun. 12, 2003 and Japanese application 2003-168614 filed Jun. 13, 2003.

TECHNICAL FIELD

The present invention relates to a contact combustion-type gas sensor installed in an environment that is easily poisoned by a sensitivity degradation substance, and its manufacturing method.

BACKGROUND ART

A solid polymer membrane-type fuel cell is, for example, provided with a stack constituted by laminating a plurality of cells in which a solid polymer electrolyte membrane is sandwiched between an anode and a cathode. Hydrogen is supplied to the anode as a fuel, and air is supplied to the cathode as an oxidizing agent, with hydrogen ions generated by the catalytic reaction in the anode passing through the solid polymer electrolyte membrane to the cathode, where an electrochemical reaction with oxygen occurs, resulting in the generation of electricity.

Moreover, in fuel cells such as a solid polymer membrane type fuel cell, although unreacted air, or off-gas, discharged from the cathode is generally exhausted to outside the system, it is necessary when doing so to check that hydrogen gas is not present in the off-gas.

As seen in Japanese Examined Patent Application Publication No. H06-52662 (hereinafter referred to as Patent Document 1) and Japanese Unexamined Patent Application Publication No. H06-223850 (hereinafter referred to as Patent Document 2), there has been developed a system in which a hydrogen detector is installed in the exhaust system of the cathode side of a fuel cell to check that hydrogen gas does not exist in off-gas.

It is conceivable for such a hydrogen detector to employ a gas contact combustion-type gas sensor, which comprises a detecting element to which a catalyst is bonded, and a temperature compensation element to which a catalyst is not bonded. Utilizing the heat of combustion when the gas to be detected (hydrogen in the case of a hydrogen detector) contacts the catalyst, the gas concentration of said gas to be detected is detected from the difference in the electrical resistance between the detecting element and the temperature compensation element.

Since organic silicon packing and hoses having heat resistance are used for the exhaust system of the cathode side, there exist in the measuring atmosphere of the contact combustion-type gas sensor small amounts of gaseous silicon compounds that precipitate and vaporize from the packing or hoses. Such silicon compounds degrade the performance of the catalyst constituting the detecting element (so-called poisoning), leading to a drop in detection sensitivity to flammable gas over time and a loss in measurement accuracy.

In order to cope with such problems, for a semiconductor sensor as seen in Japanese Unexamined Patent Application Publication No. S56-168542 (hereinafter referred to as Patent Document 3), that is, a sensor that detects changes in electrical conductivity by adsorption of a gas to be detected, by housing the sensor in an environment containing dimethylsiloxane, which exerts a poisoning action on the sensor, to age the sensor, variations in characteristics such as sensitivity between sensors are lessened.

However, no such poisoning measures have been implemented for contact combustion-type gas sensors that detect gas concentration from the difference in the electrical resistance between the detecting element and the temperature compensation element utilizing the heat of combustion when the gas to be detected (hydrogen in the case of a hydrogen detector) contacts the catalyst.

In light of these circumstances, it is a first object of the present invention to provide a contact combustion-type gas sensor that can maintain the initial sensitivity over a long period of time in the presence of silicon vapor.

It is a second object of the present invention to provide a contact combustion-type gas sensor that can minimize as much as possible the loss in sensitivity resulting from adhesion of silicon even when installed in an environment where organic silicon compounds are present.

It is a third object of the present invention to provide a manufacturing method for the aforementioned contact combustion-type gas sensor.

DISCLOSURE OF THE INVENTION

The invention for solving these problems is a contact combustion-type gas sensor consisting of a gas detecting element that is housed in a case, said gas detecting element comprising an induction portion made of an oxidation catalyst powder and an insulating powder fixed to a heater that generates Joule heat, wherein said induction portion contains not less than 30 percent by weight of said oxidation catalyst.

In one embodiment, said induction portion is formed by mixing said oxidation catalyst powder and said insulating powder with a solution and fixing the mixture onto the heater.

In another embodiment, said induction portion is formed by fixing a slurry of said insulating powder to make a solidified body of said insulating powder, while in another embodiment, the outer surface of said induction portion is formed to have a high concentration of said oxidation catalyst.

In another embodiment, an aging process is performed to converge the sensitivity loss due to silicon vapor.

In another embodiment, said aging process is performed by energizing the heater in the gas detecting element to make it generate heat.

In another embodiment, the concentration of said silicon vapor is set higher than the concentration of silicon in the environment used for measurement. In another embodiment, the contact combustion-type gas sensor is disposed in the gas outlet path on the cathodes side of the polymer-type fuel cell to detect hydrogen in an environment that contains silicon vapor and hydrogen.

In another embodiment, in a contact combustion-type gas sensor that carries a catalyst on a metal oxide sintered body carrier fixed to a resistance thermometer bulb, the contact combustion-type gas sensor is manufactured by being heated to 130° C. to 500° C. and then poisoned until fluctuations over time in the catalytic proficiency of said catalyst in an atmosphere that includes silicon compounds stabilizes to a prescribed value.

In another embodiment, said atmosphere includes between 10 parts per million (ppm) and 30,000 ppm of at least one of hexamethyldisiloxane, hexamethyldisilazane, and hexamethyldisilane.

In another embodiment, said atmosphere includes between 100 ppm and 20,000 ppm of at least one of hexamethyldisiloxane, hexamethyldisilazane, and hexamethyldisilane.

In another embodiment, said atmosphere includes between 10 ppm and 30,000 ppm of at least one of hexamethyldisiloxane, hexamethyldisilazane, and hexamethyldisilane, and between 100 ppm and 40,000 ppm of hydrogen.

In another embodiment, in a contact combustion-type gas sensor that carries a catalyst on a metal oxide sintered body carrier fixed to a resistance thermometer bulb, said metal oxide is at least one type chosen from alumina, silica, or ziolite, and poisoning is performed in advance until fluctuations over time in the catalytic proficiency of said catalyst in an atmosphere that includes silicon compounds stabilizes to a prescribed value.

In another embodiment, the contact combustion-type gas sensor is disposed in the gas outlet path on the cathode side of the polymer-type fuel cell to detect hydrogen.

Effects of the Invention

The effects of the contact combustion-type gas sensor of the present invention will be specifically explained in the following.

The invention prevents a loss in sensitivity by aging with a poisoning procedure and prevents fluctuations in the initial sensitivity during the measurement period and fluctuations in the sensitivity over time.

The invention can fix an oxidation catalyst powder and an insulating powder to a heater simultaneously, and thereby simplify the manufacturing process.

The invention can attain a specified sensitivity while reducing the amount of costly oxidation catalyst that is used.

The invention can prevent fluctuations in sensitivity due to silicon vapor in the use environment as much as possible.

The invention can efficiently heat a gas detecting element to a prescribed temperature without requiring a heat source in the ageing device.

The invention can more reliably prevent fluctuations in sensitivity over time.

The invention can detect flammable gas, such as hydrogen, without incurring fluctuations in sensitivity over time even in the presence of silicon vapor emitted from packing or tubes in the gas outlet path on the cathode side of a polymer-type fuel cell.

The invention can prevent fluctuations in the detection sensitivity for flammable gas over time even in an environment where silicon vapor is present.

The invention can improve the processing yield and shorten the processing time.

The invention can achieve more practical processing.

The invention can substantially reduce processing time by promoting the formation of silicon oxide from combustion of hydrogen on the element surface.

The invention can achieve a reduction in processing time while ensuring work safety.

The invention can stably and accurately measure the concentration of flammable gas without causing fluctuations in sensitivity over time even in an environment where silicon vapor is present.

The invention can detect flammable gas, such as hydrogen, without causing fluctuations in sensitivity over time even in the presence of silicon vapor emitted from packing or tubes in the gas outlet path on the cathode side of a polymer-type fuel cell.

The preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

BRIEF DESCRIPTION OF THE DRAWINGS

FIGS. 1(A) and (B) are perspective and sectional views, respectively showing one embodiment of the gas detecting element constituting the contact combustion-type gas sensor of the present invention.

FIGS. 8(A) and (B) are views respectively showing the state of the oxidation catalyst penetrating the pores of the metal oxide sintered body that constitutes the contact combustion-type gas sensor, and the poisoned state.

FIGS. 11(A) and (B) are graphs respectively showing the changes in the sensitivity over time in an environment of actually using the contact combustion-type gas sensor and when silicon compounds are forcefully adhered.

BEST MODE FOR CARRYING OUT THE INVENTION

The embodiments of the present invention will now be explained with reference to the drawings.

Figure 1:
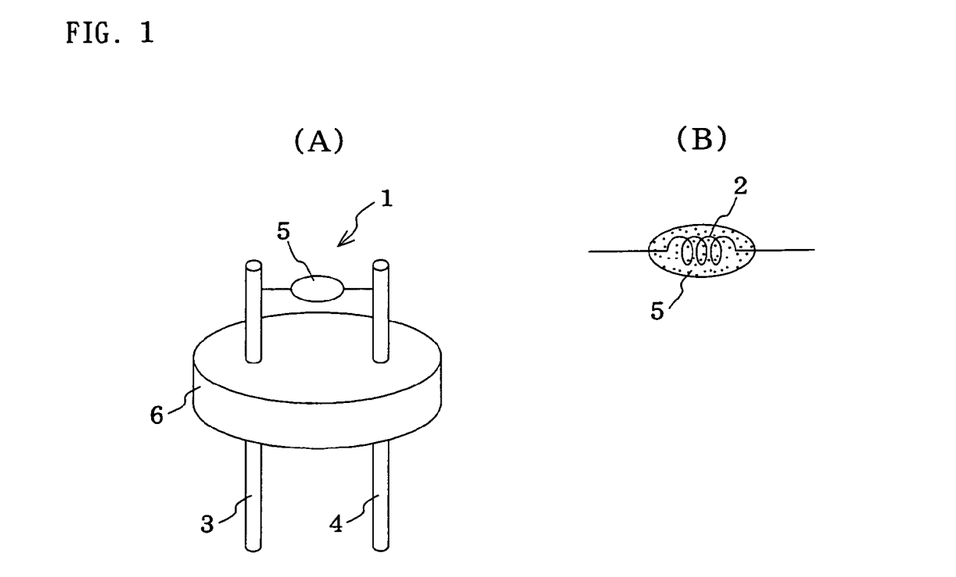

FIGS. 1(A) and (B) respectively show one embodiment of a gas detecting element 1 that constitutes the contact combustion-type gas sensor of the present invention. A heater 2, which is a resistance wire having heat resistance and corrosion resistance formed into a coil shape, is stretched between stays 3 and 4 which also function as leads. Around the heater 2 is formed an induction portion 5 by mixing an oxidation catalyst powder and an insulating powder of a predetermined composition with a liquid such as water to make a slurry, dripping the slurry onto the heater 2 to form a spherical shape, solidiing it by natural drying, and then sintering it.

Reference number 6 in the drawing denotes a base that fixes the stays 3 and 4 and attaches to a case described later.

One or a plurality of types of oxidation catalyst powder is chosen from platinum (Pt), palladium (Pd), platinum oxide (PtO) and palladium oxide (PdO) that is processed into fine powder by passing through a grinding step or the like. The oxidation catalyst powder is mixed with heat-resistant insulating powder such as alumina and silicon oxide to not less than 30 percent by weight and preferably not less than 40 percent by weight.

The gas detecting element 1 constituted thus is housed in an atmosphere including in the form of a vapor at not less than 10 ppm a material that exerts a poisoning action on the oxidation catalyst; such as silicon, at a concentration higher than the actual measuring environment. Aging of the induction portion 5 is performed for a specified time, such as 2 hours, by heating to a range between 180° C. and 500° C. by means of Joule heat generated from the heater 2 by energizing the stays 3 and 4.

Since the speed in which the aging advances greatly depends on the temperature of the induction portion 5, setting the temperature of the induction portion 5 higher can shorten the aging time.

Thus, the silicon vapor present in the environment reacts with the oxidation catalyst of the induction portion 5 to become silicon dioxide that adheres to the surface of the induction portion 5. At the stage when the specified time has elapsed, energizing of the stays 3 and 4 is stopped, and the induction portion 5 is removed from the aging environment.

To investigate the concentration of the oxidation catalyst powder in the induction portion 5 of the gas detecting element 1 and the sensitivity to flammable gas from said aging process, as shown in Table 1, samples were prepared in which the oxidation catalyst powder content of the induction portion 5 was altered. These samples were then aged for 20 hours in an atmosphere in which hexamethyldisiloxane is present as a silicon vapor at 2,000 ppm.

TABLE 1

| Symbol | Insulating Powder Al$_2$O$_3$ (wt %) | Oxidation Catalyst Powder | | Total Catalyst Quantity (wt %) |
| --- | --- | --- | --- | --- |
| | | Pd (wt %) | Pt (wt %) | |
| ● | 92 | 7 | 1 | 8 |
| ■ | 82 | 13 | 5 | 18 |
| ○ | 67 | 22 | 11 | 33 |
| □ | 45 | 45 | 10 | 55 |
| △ | 0 | 80 | 20 | 100 |

Figure 2:
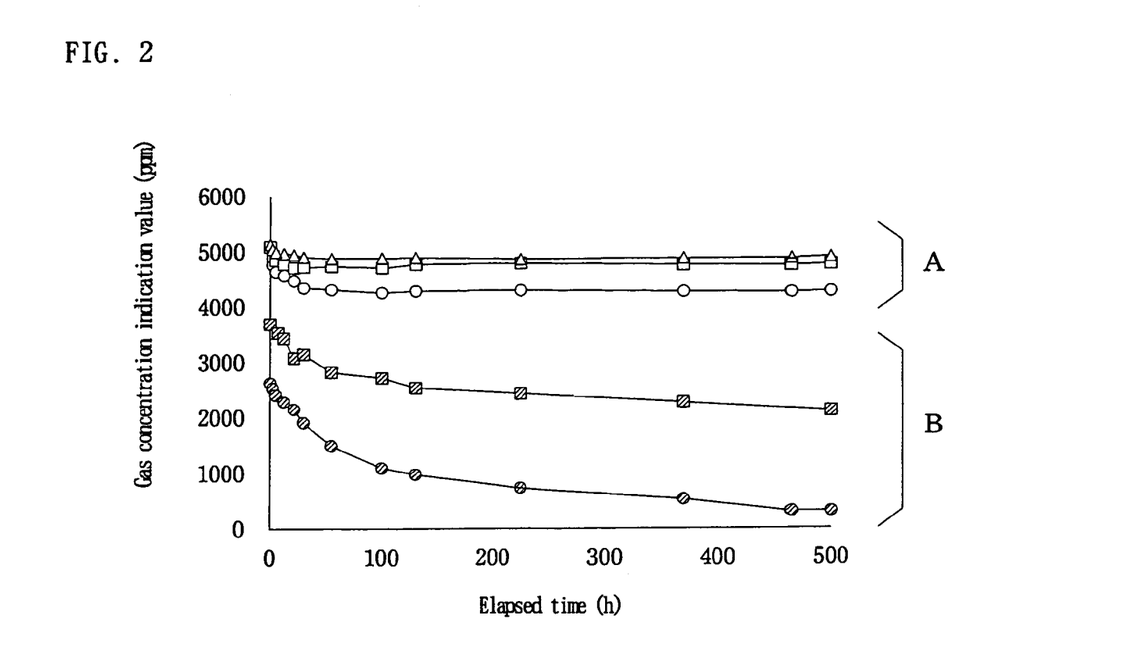
FIG. 2 is a graph showing changes in sensitivity over time in an environment including a poisoning substance after performing aging processing in an atmosphere containing a high concentration of a poisoning substance on a gas detecting element, manufactured by altering the concentration of oxidation catalyst powder contained in the induction portion.

FIG. 2 shows changes in sensitivity in an environment containing silicon vapor after adjusting the initial indicated value of the gas detecting element manufactured in the aforementioned process to a specified value. In the graph, Group A shows the characteristics of the gas detecting element in which the concentration of the oxidation catalyst powder in the induction portion 5 is not less than 30 percent by weight and preferably not less than 40 percent by weight, and group B shows the characteristics of the gas detecting element in which the oxidation catalyst powder in the induction portion 5 is not more than 30 percent by weight. As is clear from FIG. 2, for the gas detecting element in which the concentration of the oxidation catalyst powder in the induction portion 5 is not less than 30 percent by weight and preferably not less than 40 percent by weight, the decrease in sensitivity was extremely small, as is also evident from the curve of group A. In contrast, for the gas detecting element in which the oxidation catalyst powder in the induction portion 5 is not more than 30 percent by weight, not only did the sensitivity fall rapidly at the early stages as shown in the group B of FIG. 2, but the sensitivity fell over time as well.

Figure 3:
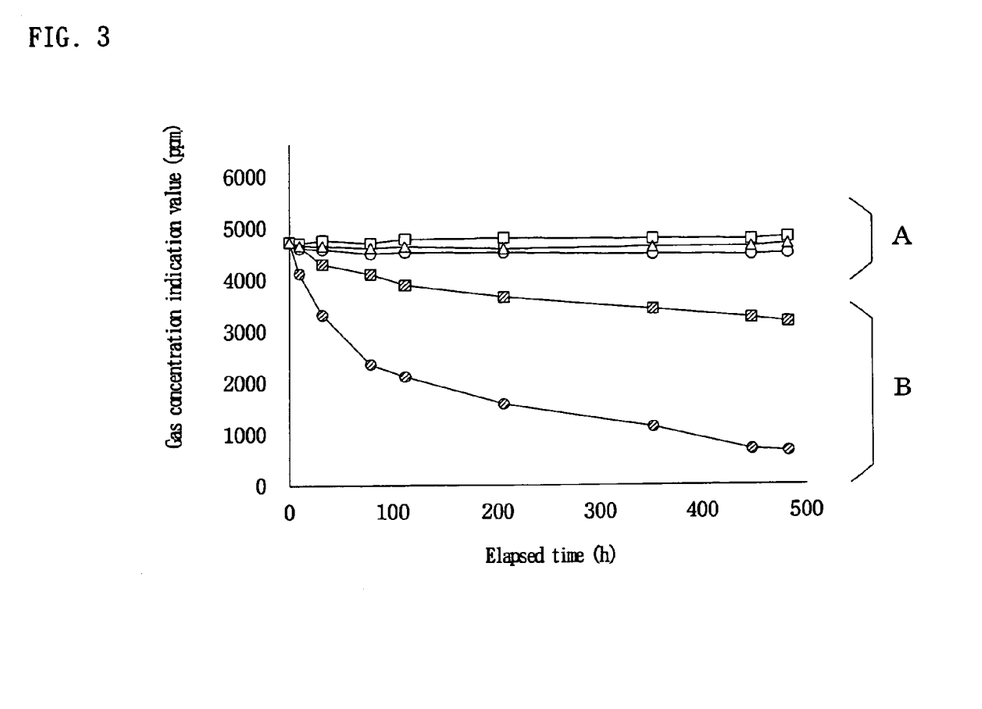
FIG. 3 is graph showing changes in sensitivity over time in an environment including a poisoning substance for a gas detecting element manufactured by altering the concentration of oxidation catalyst powder contained in the induction portion.

Meanwhile, FIG. 3 shows the results of investigating fluctuations in sensitivity in an environment containing silicon vapor after adjusting the initial indicated value of the gas detecting element manufactured in the aforementioned process to a specified value without performing the aforementioned aging process on the gas detecting element shown in the aforementioned Table 1.

That is, group A in FIG. 3 shows the characteristics of the gas detecting element in which the concentration of the oxidation catalyst powder in the induction portion 5 is not less than 30 percent by weight and preferably not less than 40 percent by weight, and group B shows the characteristics of the gas detecting element in which the oxidation catalyst powder in the induction portion 5 is not more than 30 percent by weight. As is evident from FIG. 3, a gas detecting element that contains an oxidation catalyst powder concentration of not less than 30 percent by weight and preferably not less than 40 percent by weight has an extremely small drop in sensitivity, as also seen from the curve of group A. In contrast, for the gas detecting element in which the oxidation catalyst powder in the induction portion 5 is not more than 30 percent by weight, not only did the sensitivity fall rapidly at the early stages as shown in group B of FIG. 3, but the sensitivity fell over time as well.

From this it is found that setting the concentration of the oxidation catalyst powder to not less than 30 percent by weight and preferably not less than 40 percent by weight can prevent a decease in the initial sensitivity due to silicon vapor and maintain the sensitivity at a stable, high level over a long period of time regardless of whether aging is performed in the presence of silicon vapor.

Figure 4:
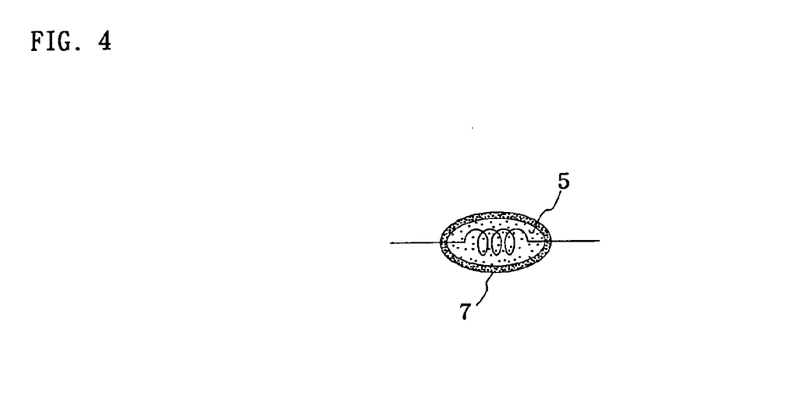
FIG. 4 is a sectional view showing another embodiment of the gas detecting element that constitutes the contact combustion-type gas sensor of the present invention.

FIG. 4 shows an embodiment of the gas detecting element, wherein on the surface of the induction portion 5 described in the aforementioned embodiment there is further formed a catalyst layer 7 by applying a slurry consisting only of an oxidation catalyst powder, and sintering it.

The gas detecting element constituted thus is placed in the same environment as described above, and then aging is performed by heating the induction portion 5 to between 180° C. and 500° C. with Joule heat generated from the heater 2 by energizing the stays 3 and 4.

According to this embodiment, since the oxidation catalyst powder has a smaller grain size than the heat-resistant insulating substance and silicon adheres to the oxidation catalyst powder, the surface region functions to filter silicon with a relatively large molecular weight, thereby preventing silicon in the measurement environment from invading the induction portion 5, and so more reliably restricting reductions in sensitivity.

In the aforementioned embodiment, aging was performed on the gas detecting element 1, but the same effect is exhibited even if aging is performed in the state of being housed in a case and assembled into the contact combustion-type gas sensor.

In the aforementioned embodiment, the induction portion 5 was constituted by dripping a mixed slurry of the oxidation catalyst powder and the insulating powder onto the heater 2, forming a solidified body, and then sintering it. However, the same effect is exhibited even if sintering is done after forming a solid in a two-step process by dripping only a slurry of the insulating powder onto the heater 2 to form a solid, sintering it, and then dripping a slurry of the oxidation catalyst powder thereon.

Since doing so can selectively impregnate the oxidation catalyst powder at a high concentration near the surface where the gas to be detected makes contact, a cost savings is achieved and sensitivity fluctuations due to silicon vapor can be minimized as much as possible by raising the concentration of the oxidation catalyst at the induction region.

Figure 5:
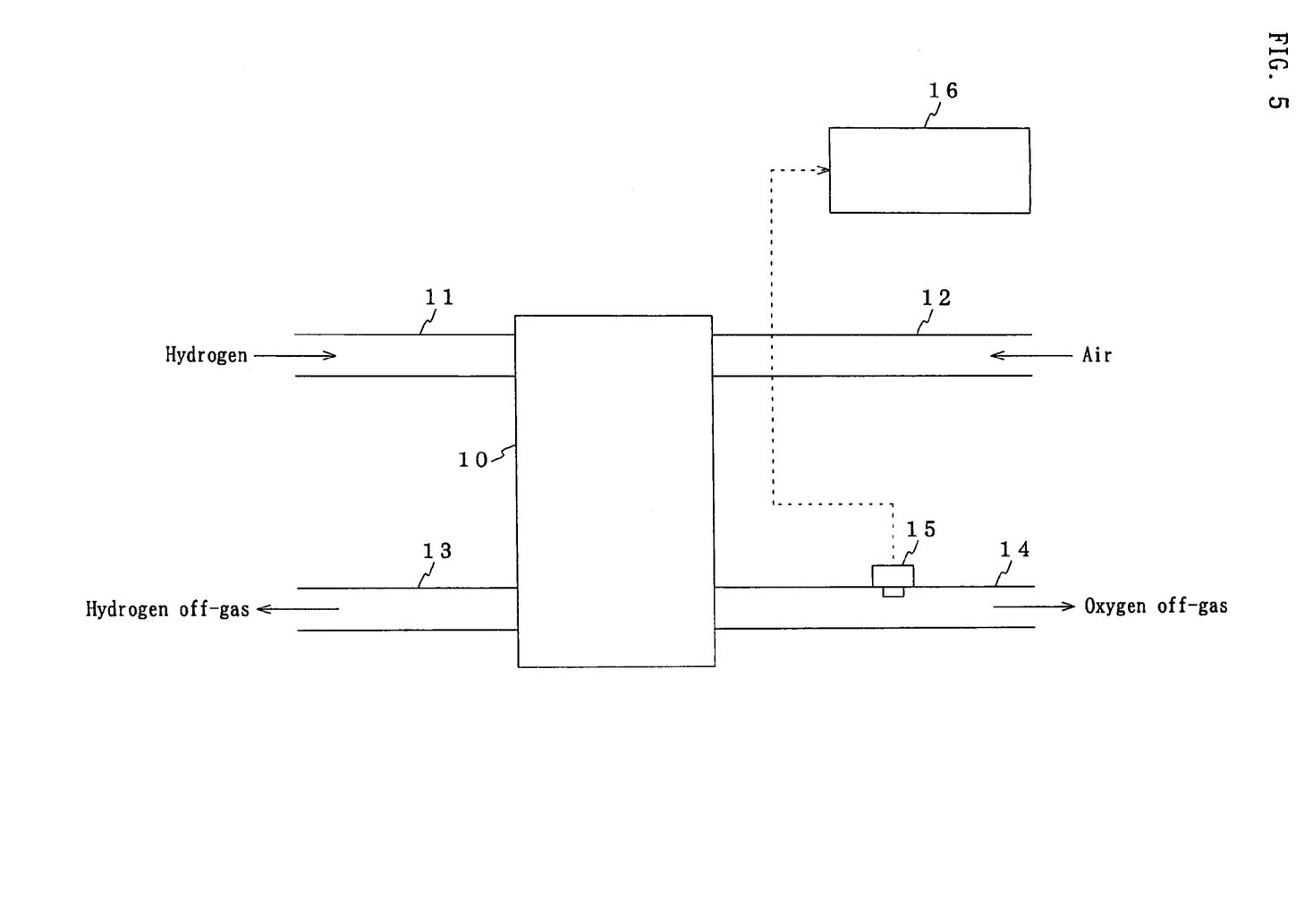
FIG. 5 is a schematic drawing of the fuel cell system which is an example of applying the contact combustion-type gas sensor of the present invention.

Incidentally, the built-in heater-type gas sensor described above is particularly effective in detecting flammable gas, such as hydrogen, in the exhaust pipe of the fuel cell system shown in FIG. 5.

A fuel cell 10 is constituted by laminating a plurality of groups of fuel cells not illustrated, each consisting of an electrolyte electrode structure in which an electrolyte such as a solid polymer electrolyte membrane is sandwiched between an anode electrode and a cathode electrode and further sandwiched between a pair of separators. Fuel gas such as hydrogen supplied from an inlet side path 11 on the anode side electrode is ionized by a catalytic electrode and moved to the cathode side electrode via the solid polymer electrolyte membrane that is moderately humidified. Electrons that are given off during this period are diverted to an external circuit to be utilized as direct current electrical energy. Since oxidizer gas such as oxygen or air is supplied to the cathode side electrode via an inlet side path 12, water is produced at the cathode side electrode by the reaction of the hydrogen ions, electrons and oxygen. Then, at the cathode side, so-called off gas is discharged to outside the system from outlet side paths 13, 14 on the anode side and cathode side, respectively.

Here, a contact combustion-type gas sensor 15 of the present invention, to which a poisoning procedure has been applied, is installed at the outlet side path 14 of the cathode side, and confirmation that hydrogen gas has not been discharged from the outlet side path 14 of the cathode side is performed by a monitoring device 16.

According to this embodiment, even if organic silicon packing and hoses are used for the outlet side path 14 on the cathode side that reaches a high temperature compared to other gas paths, hydrogen gas can be detected without causing changes in sensitivity over time.

A second embodiment of the contact combustion-type gas sensor of the present invention will now be described in detail.

The contact combustion-type gas sensor of the present invention supports a catalyst on a carrier made of a metal oxide sintered body adhered to a resistance thermometer bulb. As a metal oxide used for this element, at least one kind chosen from alumina, silica, or zeolite is given.

In the present invention, zeolite is preferable from the aspect of easily controlling the pore diameter of the metal oxide sintered body. Also, as the oxidation catalyst used for the contact combustion-type gas sensor, one is suitably selected from the group of platinum, ruthenium, palladium, and rhodium depending on the type of flammable gas to be detected.

Figure 6:
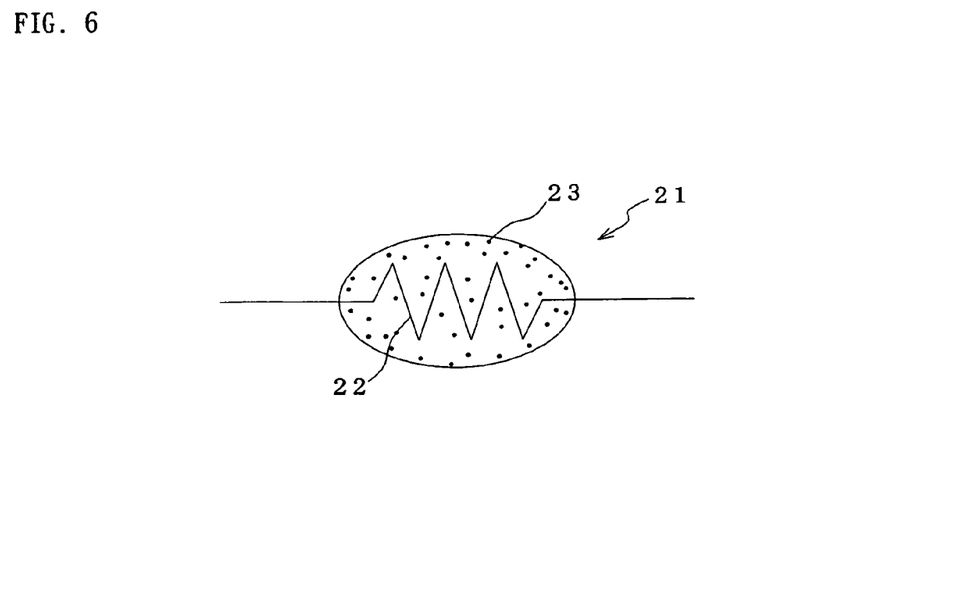
FIG. 6 is a sectional view showing another embodiment of the contact combustion-type gas sensor before the poisoning process employed in the present invention.

FIG. 6 shows an example of the contact combustion-type gas sensor as a basic element. A contact combustion-type gas sensor 21 consists of, for example, a platinum wire with a diameter of 60 µm wound 10 times with an outer diameter of 0.6 mm to produce a resistance thermometer bulb 22 that also functions as a coil heater with a length of 1.5 mm. Next, an alumina, silica, or zeolite paste is stuck to the resistance thermometer bulb 22, which is then fired at 800° C. to form a porous metal oxide sintered body 23 having electrical insulation on the platinum coil.

Here, the pore diameter of the metal oxide sintered body 23 is preferably smaller than the organic silicon and greater than a flammable gas molecule, an oxygen molecule, and a water molecule.

Figure 7:
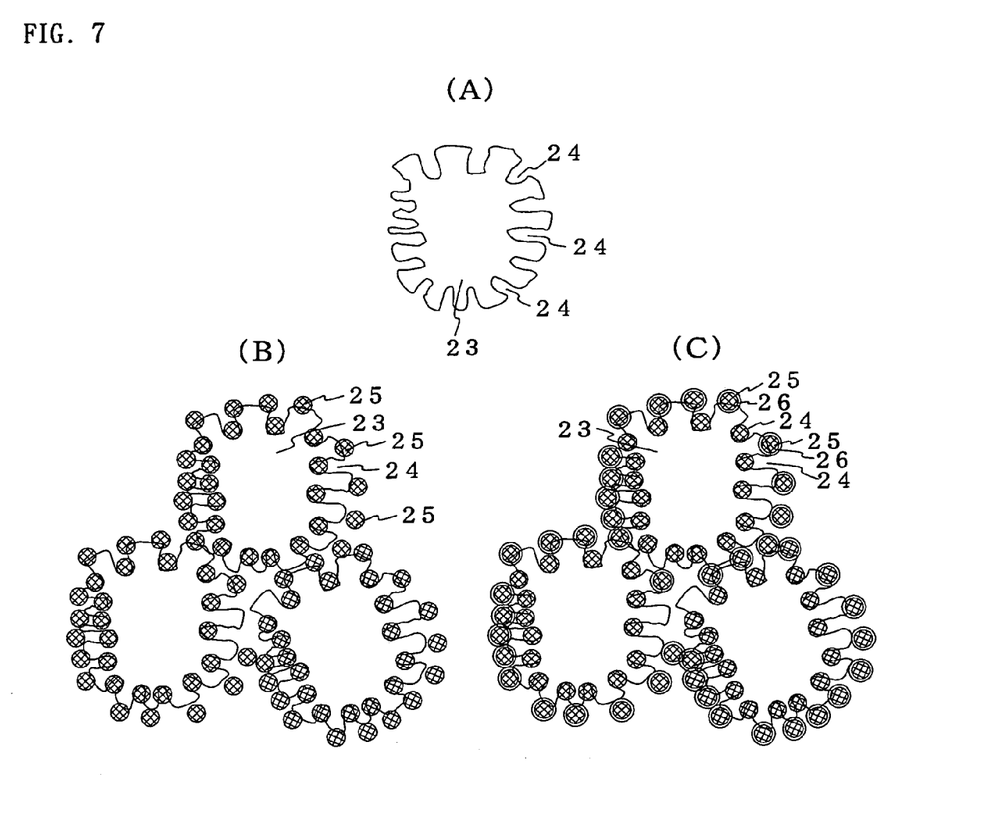
FIGS. 7(A) to (C) are views respectively showing pores of the metal oxide. sintered body that constitutes the contact combustion-type gas sensor, the state of the oxidation catalyst adhered to the metal oxide sintered body, and the poisoned state.

The metal oxide sintered body 23 is then immersed in a platinum chloride acid solution, and the platinum chloride acid solution is made to impregnate pores 24 (FIG. 7 (A)) of the metal oxide sintered compact 23 (FIG. 7(B)). When the impregnation is sufficiently completed, the metal oxide sintered body 23 is raised, heating decomposition is carried out at 600° C. so that catalyst particles 25 of a platinum catalyst are carried on the pores 24 and the surface of the metal oxide sintered body 23.

Since the contact combustion type gas sensor 21 constituted in this way has pores 24 that are smaller than the organic silicon and greater than a flammable gas molecule, an oxygen molecule, and a water molecule, flammable gas molecules and oxygen molecules can reach the catalyst particles 25 being carried in the pores 24 of the metal oxide sintered body 23.

On the other hand, organic silicon adheres to the surface of the catalyst particles 25 that are fixed to the surface of the metal oxide sintered body 23 (FIG. 7(C)).

Figure 8:
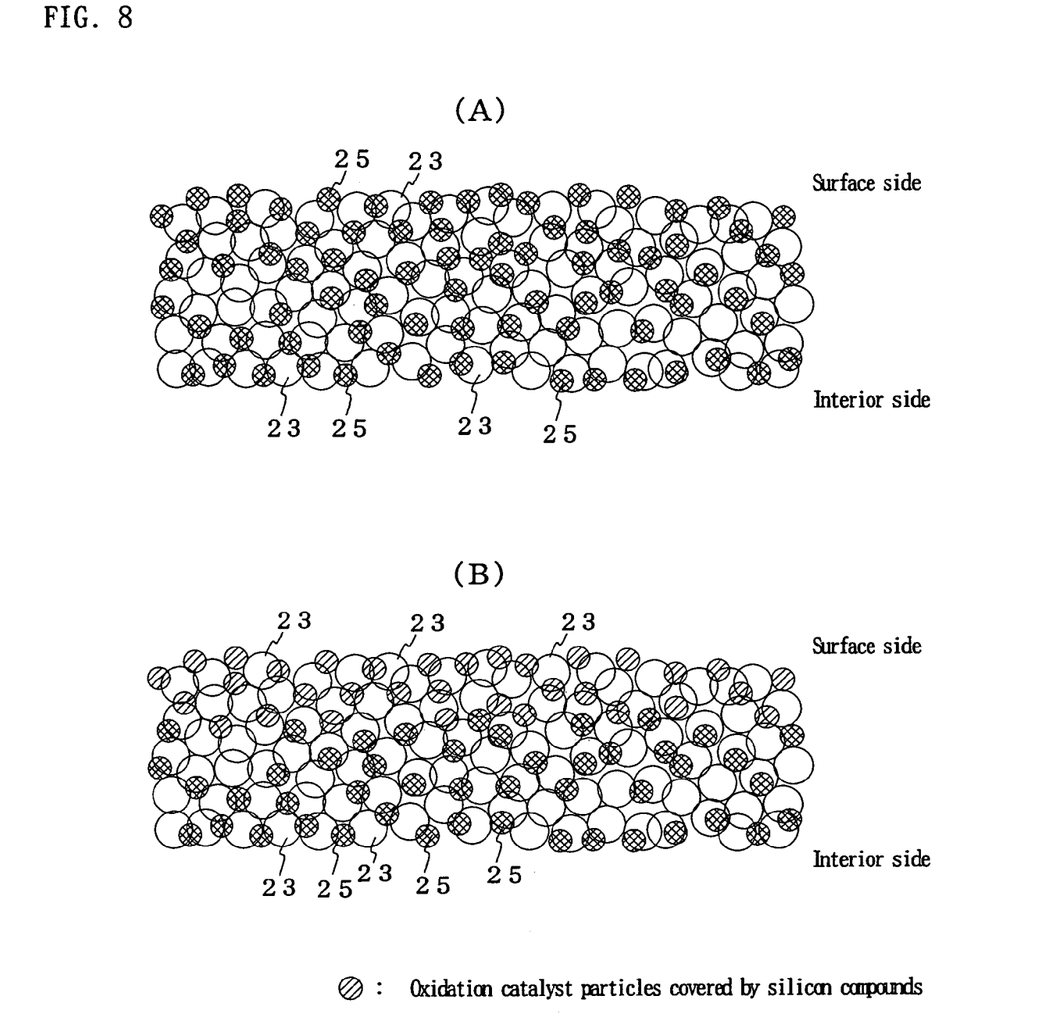

The aforementioned embodiment described the case of catalyst particles 25 impregnating the pores of each particle of the metal oxide sintered body 23. However, as shown in FIG. 8(A), since the organic silicon can permeate only into the region near the surface (the top side in the drawing) in the mode of the catalyst particles 25 permeated into gaps formed between particles of the metal oxide sintered body, only- the catalyst particles 25 on the surface are covered by organic silicon.

Figure 9:
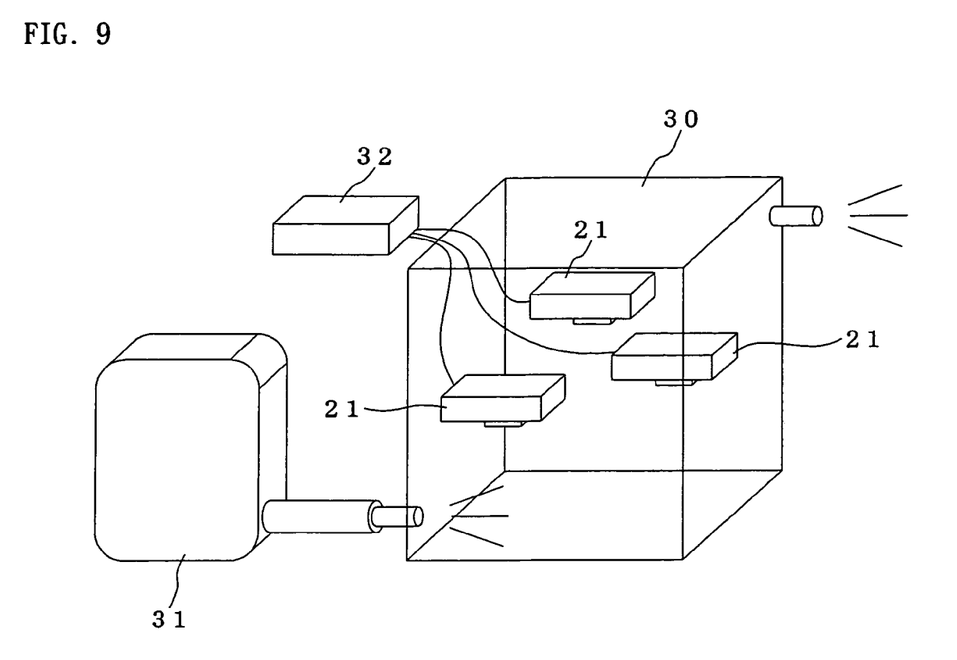
FIG. 9 is a view showing an embodiment of the device for performing poisoning of the contact combustion-type gas sensor.

The base of the contact combustion-type gas sensor 21 constituted in this way is accommodated in a process chamber 30 as shown in FIG. 9. Organic silicon such as hexamethyldisiloxane or hexamethyldisilazane, which is the poisoning component, is supplied to this space from a vaporizer at a concentration of 10 to 1,000 ppm. Electric power is simultaneously supplied from a power unit 32 to the resistance thermometer bulb 22 of the contact combustion-type gas sensor 21 to heat to between 130° C. and 500° C. the contact combustion-type gas sensors 21 to be processed.

In addition, the organic silicon must be easy to obtain industrially, and have a vapor pressure sufficient for reaching a concentration necessary for the processing. Table 2 shows examples of the organic silicon.

TABLE 2

| Organic Silicon Compound | Boiling Point (° C.) | Gasifiable concentration (%) at normal temperature |
|---|---|---|
| Tetraethoxysilane | 166 | 0.2 |
| Octamethylcyclotetrasiloxane | 175 | 0.1 |
| Tetramethylsilane | 26.5 | 73.7 |
| Trimethylsilane | 6.7 | 100 |
| Tetramethylcyclotetrasiloxane | 135 | 0.9 |
| Hexamethyldisilane | 113 | 3.0 (estimate) |
| Hexamethyldisilazane | 125 | 1.6 (estimate) |
| Hexamethyldisiloxane | 101 | 5.3 |
| Dimethyldimethylaminosilane | 67 | 19.7 |
| Dimethyldimethoxysilane | 81.4 | 11.8 |

Figure 10:
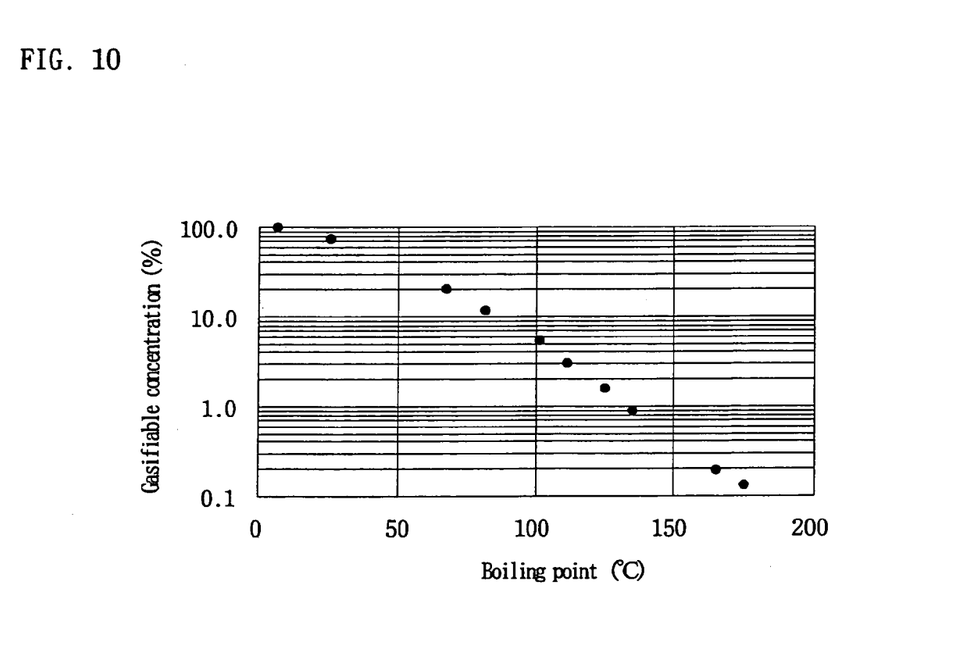
FIG. 10 is graph showing the relation between the boiling point and the gasifiable concentration by temperature.

As shown in FIG. 10, there is a correlation between the boiling point of organic silicon and the concentration at which it is gasifiable at an normal temperature, in that as the-boiling point rises it does not gasify until reaching a specified concentration. The organic silicon easily gasifies as the boiling point decreases, but does not gasify even at a normal temperatures, and so handling is not easy. Hexamethyldisiloxane, 10 hexamethyldisilazane, and hexamethyldisilane, which are in a range of 50° C. to 150° C., are readily obtainable and can be easily adjusted to the concentration required for processing.

Moreover, in the case of the concentration of the organic silicon being 10 ppm or less, not only does the time to the completion of processing, that is, the time until the sensitivity drop reaches the converging point, become longer, but since the quantity of organic silicon decreases, measurement errors easily arise, leading to a drop in the processing yield.

Meanwhile, when the organic silicon concentration exceeds 30,000 ppm, the evaporation rate of the organic silicon is significantly influenced by the temperature, which leads to a drop in the processing yield.

Accordingly, the lower limit of the organic silicon concentration is 10 ppm and the upper limit is 30,000. However, in consideration of accuracy and ease of adjusting the atmosphere, and moreover the manufacturing yield, the organic silicon concentration is preferably between 100 ppm and 20,000 ppm.

Since the catalytic action of an oxidation catalyst is low when the temperature is 130° C. or less, the decomposition rate of organic silicon is also low, so that adhesion of a silicon compound 26 to the surface of the metal oxide sintered body 23 does not advance. On the other hand, if the temperature is 500° C. or more, sintering of the metal oxide sintered body 23 will arise, causing the catalytic action of the oxidation catalyst to fall.

The organic silicon is thus decomposed on the surface of the metal oxide sintered body 3 heated to several hundred degrees, and as shown in FIG. 7(C) and FIG. 8(B) becomes-a silicon compound 26 that adheres in a laminar form. When removed from the process chamber 10 after the predetermined time, the contact combustion-type gas sensor 1' of the present invention is complete. When the above-mentioned silicon compound 26 is analyzed by X-ray electron spectroscopy, it is confirmed as being silicon dioxide.

In addition, although the processing time is influenced by the concentration and temperature of the organic silicon, since it is a value uniquely determined by these parameters, the processing time can be determined by prior experimentation.

Although that portion of the oxidation catalyst which is exposed to the surface of the contact combustion-type gas sensor 21' constituted in this way is covered by the silicon compound 26, thereby losing its catalytic function, entry of organic silicon is impeded by the silicon compound 26 formed on the surface of the sensor 21'. Moreover, since the pores 24 of the metal oxide sintered body 23 are smaller than the silicon compound 26 and larger than a flammable gas molecule, an oxygen molecule, and a water molecule, the catalyst particles 25 positioned inside the pores 24 are presumed to be able to maintain their function as an oxidation catalyst.

For the purpose of comparison, the contact combustion-type gas sensor 1 before processing and the contact combustion-type gas sensor 21' after processing were disposed in an environment in which organic silicon is present to investigate changes in the sensitivity to detecting flammable gas over time; As shown by line A in FIG. 11(A), there was hardly any change over time in the detection sensitivity of the contact combustion-type gas sensor 21' of the present invention.

Figure 11:
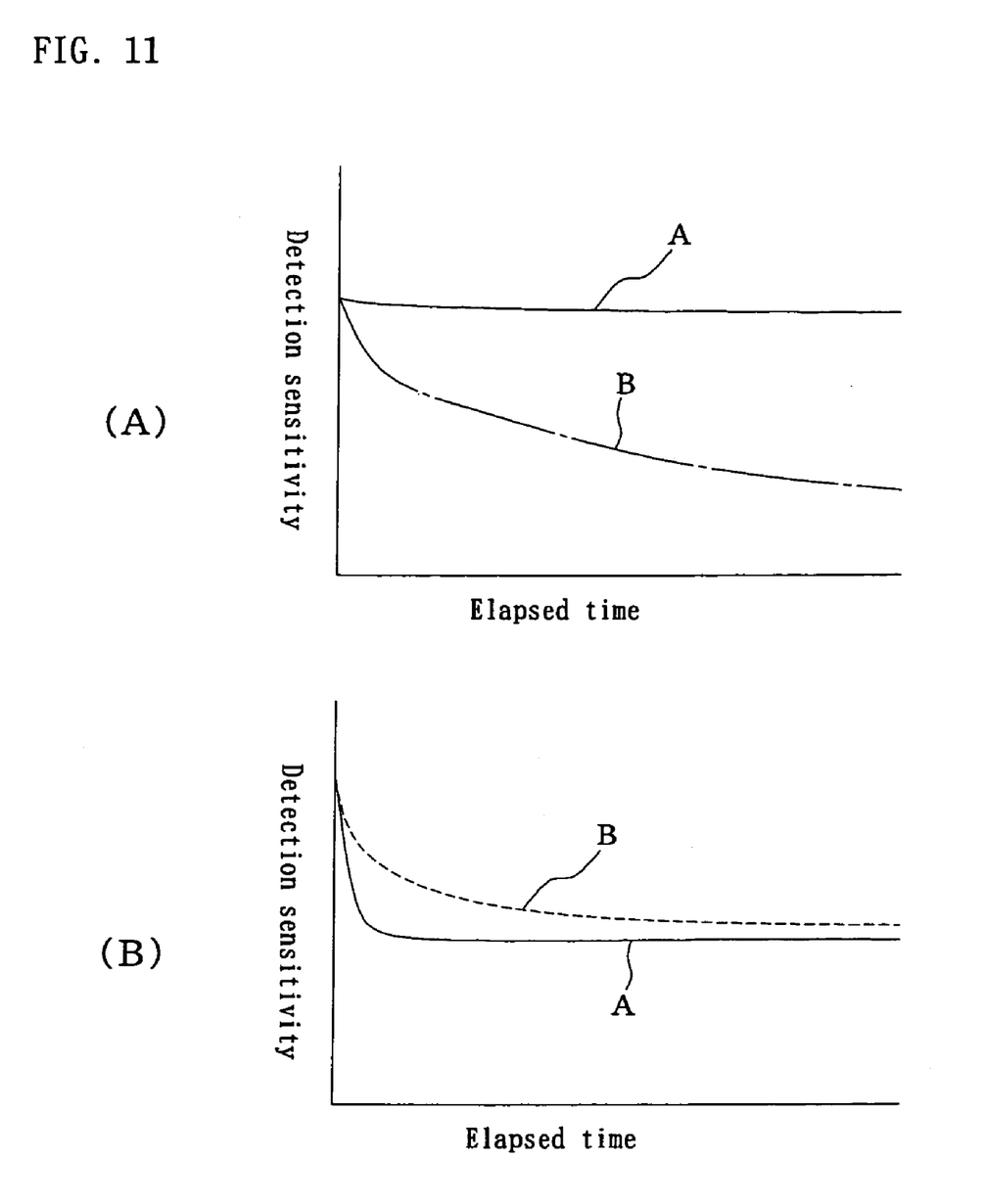

On the other hand, the oxidation catalyst layer does not have a pore diameter that is smaller than the organic silicon and larger than a flammable gas molecule, an oxygen molecule, and a water molecule. Also, in the contact combustion-type gas sensor 21 to which the aforementioned processing is not applied, the tendency of the sensitivity to slowly decrease over time continues without converging at a steady value, that is, without settling at a steady value.

In the aforementioned embodiment, processing is performed in the environment in which organic silicon is present, but when processing is executed in an environment in which hydrogen is added; the detection sensitivity decreases in a short time to a specified sensitivity as shown by line A in FIG. 11(B). This is-presumed to happen because, when processing is executed in an environment in which organic silicon and hydrogen are present, hydrogen contained in the atmosphere will combust on the surface due to the oxidation catalyst of the contact combustion-type gas sensor 1, and so the surface temperature of the contact combustion-type gas sensor 1 becomes higher than the case when heated only by a resistance thermometer bulb (that is, a state without an oxidation catalyst), thereby promoting the adhesion of organic-silicon.

Line B in FIG. 11(B) shows the drop in sensitivity due to processing in an atmosphere in which hydrogen is not added.

If the amount of hydrogen added has a concentration of 100 ppm to 40,000 ppm with respect to 10 to 30,000 ppm for organic silicon vapor, such as hexamethyldisiloxane or hexamethyldisilazane, the silicon compound 6 can be generated safely and in a short time even if hydrogen, a flammable gas, is used.

When the hydrogen concentration is 100 ppm or less, similarly to when the organic silicon concentration is extremely low, the time until the completion of processing, that is, the time until the sensitivity drop settles at a fixed value, or, reaches the converging point, becomes longer. Also, it is not desirable for the hydrogen concentration to exceed 40,000 ppm on grounds of work safety, since the lean flammability limit is exceeded.

In consideration of these matters, the hydrogen concentration is between 100 ppm and 40,000 ppm, and in consideration of safety and processing efficiency, more preferably between 1,000 ppm and 20,000 ppm.

In addition, although the time to the completion of processing is influenced by the concentration and temperature of the organic silicon and hydrogen, since it is a value uniquely determined by these parameters, the processing time can be determined by prior experimentation.

If the above-mentioned contact combustion-type gas sensor 21' is placed in an environment in which organic silicon is mixed to detect flammable gas, such as hydrogen, then oxygen and the flammable gas will pass through the pores 24 of the metal oxide to reach the catalyst 25 and ignite, producing the predetermined output. Meanwhile, since the substance which serves as organic silicon is impeded by the silicon compound 26 formed in advance on the surface of the sensor 1', and, moreover, the diameter of the pores 24 of the metal oxide sintered body 23 is smaller than the organic silicon, it is presumed not to be able to enter as far as the catalyst particles 25 positioned inside the pores 24, and so does not cause a drop in sensitivity.

As mentioned above, compared with the contact combustion-type gas sensor with no poisoning treatment, the decrease in sensitivity of the sensor of the present invention is extremely small, and so the detection sensitivity at the start of usage can be stably maintained over a long period.

The aforementioned embodiment was constituted by forming the metal oxide sintered body to enclose a coiled resistance wire, but it is clear that the same action is exhibited even if applied to a sensor in which the metal oxide sintered body is formed in a laminar form on the surface of a plate-shaped heater.

Incidentally, the aforementioned sensor with the built-in heater is particularly effective for detecting flammable gas, such as hydrogen, in the exhaust pipe of the fuel cell system shown in FIG. 5.

According to this embodiment, similarly to the aforementioned embodiment, even if organic silicon packing and hoses are used for the outlet side path 14 on the cathode side that reaches a high temperature compared to the other gas path, hydrogen gas can be detected without causing changes in sensitivity over time.

Since it has few drops and fluctuations in sensitivity due to silicon in the atmosphere, the contact combustion-type gas sensor of the present invention can detect flammable gas such as hydrogen without causing fluctuations in sensitivity over time even when in an environment in which silicon vapor emitted from packing and tubes is present due to high temperature such as found in the gas outlet path on the cathode side of a polymer-type fuel cell.

What is claimed is:

1. A contact combustion-type gas sensor consisting of a gas detecting element that is housed in a case, said gas detecting element comprising an induction portion made of an oxidation catalyst powder and an insulating powder fixed to a heater that generates Joule heat, wherein said induction portion contains not less than 30 percent by weight of said oxidation catalyst, and wherein the surface of the induction portion is coated with a silicon dioxide laminar formed by an process.

2. The contact combustion-type gas sensor according to claim 1, wherein said induction portion is formed by mixing said oxidation catalyst powder and said insulating powder with a solution and fixing the mixture onto the heater.

3. The contact combustion-type gas sensor according to claim 1, wherein said induction portion is formed by fixing a slurry of said insulating powder to make a solidified body and then fixing a slurry of said oxidation catalyst powder to the solidified body of said insulating powder.

4. The contact combustion-type gas sensor according to claim 1, wherein the outer surface of said induction portion is formed to have a high concentration of said oxidation catalyst.

5. The contact combustion-type gas sensor according to claim 1, wherein said oxidation catalyst comprises one type or a plurality of types chosen from platinum, (Pt), palladium (Pd), platinum oxide (PtO) and palladium oxide (PdO).

6. The contact combustion-type gas sensor according to claim 1, wherein the aging process converges the sensitivity loss due to silicon vapor.

7. The contact combustion-type gas sensor according to claim wherein said aging process is performed by energizing the heater in the gas detecting element to make it generate heat.

8. The contact combustion-type gas sensor according to claim 6, wherein the concentration of said silicon vapor is set higher than the concentration of silicon in the environment used for measurement.

9. The contact combustion-type gas sensor according to claim 6, wherein said aging process is set to a temperature higher than the operating temperature of said gas detecting element.

10. The contact combustion-type gas sensor according to claim 1, wherein the contact combustion-type gas sensor is disposed in the gas outlet path on the cathode side of a polymer-type fuel cell to detect hydrogen in an environment that contains silicon vapor and hydrogen.

* * * * *